United States Patent [19]
Fothergill et al.

[11] 3,972,900
[45] Aug. 3, 1976

[54] 7-SUBSTITUTED BENZOFURAN DERIVATIVES

[75] Inventors: Graham Alwyn Fothergill, Knebworth; John Mervyn Osbond, Hatfield; James Charles Wickens, St. Albans, all of England

[73] Assignee: Hoffmann-La Roche Inc., Nutley, N.J.

[22] Filed: Sept. 15, 1975

[21] Appl. No.: 613,687

[30] Foreign Application Priority Data
Sept. 26, 1974  United Kingdom............... 41890/74
Aug. 29, 1975  United Kingdom............... 41890/74

[52] U.S. Cl.............. 260/346.2 R; 424/285; 260/307 A; 260/340.9

[51] Int. Cl.² .................................... C07D 307/81
[58] Field of Search ........................... 260/346.2 R

[56] References Cited
UNITED STATES PATENTS
3,340,266   9/1967   Howe et al. .................. 260/346.2 R

*Primary Examiner*—Natalie Trousof
*Assistant Examiner*—Bernard Dentz
*Attorney, Agent, or Firm*—Samuel L. Welt; George M. Gould

[57] ABSTRACT

The present disclosure is concerned with new benzofuran derivatives and a process for the preparation thereof. The present benzofuran derivatives are useful as β-adrenergic blocking agents.

7 Claims, No Drawings

7-SUBSTITUTED BENZOFURAN DERIVATIVES

DESCRIPTION OF THE INVENTION

The benzofuran derivatives provided by the present invention are compounds of the formula

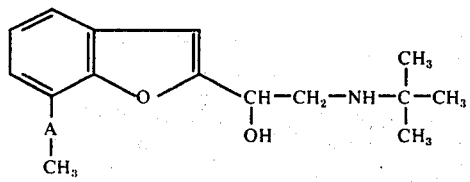

, wherein A is hydroxymethylene (CH—OH) or carbonyl (C=O), and acid addition salts thereof.

According to the process provided by the present invention, the benzofuran derivatives aforesaid (i.e. the compounds of formula I hereinbefore in which A is hydroxymethylene and their acid addition salts) are prepared by a. treating a compound of the formula

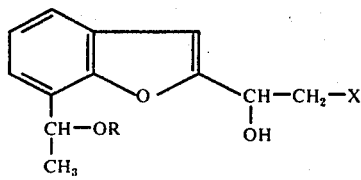

, wherein R is hydrogen or lower alkanoyl and X is chlorine or bromine, with tertbutylamine, or b. reducing a compound of the general formula

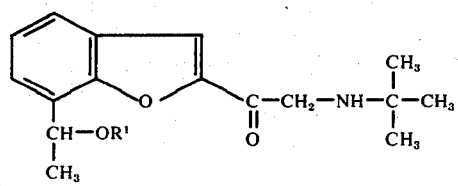

, wherein $R^1$ is lower alkanoyl with an alkali metal borohydride, or c. catalytically hydrogenating a compound of the general formula

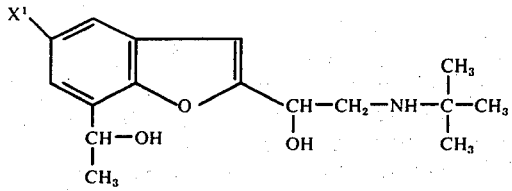

, wherein $X^1$ is chlorine or bromine.

Compounds of formula I where A is carbonyl may be prepared as follows:

d. treating a compound of the formula

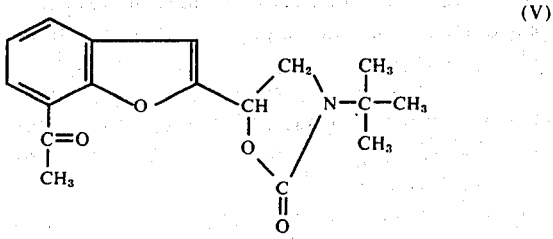

with a base, or e. oxidizing a compound of formula I in which A is hydroxymethyl with a chromic oxidizing agent, and, if desired, in any of the above processes (a)–(e) converting a compound of formula I obtained into an acid addition salt.

In accordance with embodiment (a) of the process aspect of the invention, a compound of formula II is treated with tertbutylamine. In formula II, the symbol R is hydrogen atom or lower alkanoyl. The term "alkanoyl" as used herein is meant to include groups containing up to seven carbon atoms such as acetyl, propionyl, butyryl etc. R preferable is acetyl. Also, in formula II the symbol X preferably represents a bromine atom. The treatment of a compound of formula II with tertbutylamine can suitable be carried out by heating a compound of formula II with tertbutylamine in an inert organic solvent, preferably a polar solvent such as a lower alkanol (e.g. methanol, ethanol etc), acetonitrile or dimethylformamide at an elevated temperature (e.g. the reflux temperature of the mixture). The treatment can be carried out in the presence of an acid-binding agent if desired, suitable acid-binding agents being, for example, alkali-metal carbonates (e.g. sodium carbonate) and tertiary organic amines (e.g. pyridine). An excess of tertbutylamine can be used and can then serve as the acid-binding agent.

The foregoing treatment leads, as a rule, to a mixture of a desired compound of formula I in which A is hydroxymethylene and a compound of the formula

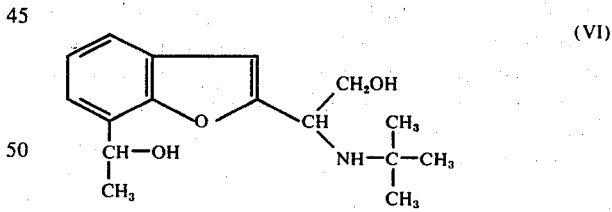

This mixture can be readily separated into its components by conventional techniques; for example, by fractional crystallization of appropriate salts (e.g. oxalates).

In accordance with embodiment (b) of the presence process, a compound of formula III is reduced using an alkali metal borohydride, preferably sodium borohydride. This reduction is suitably carried out at a temperature of ca 20°C or below. It is preferred to carry out the reduction in a lower alkanol (e.g. ethanol) or aqueous dioxane, but other solvents which are inert under the conditions of the reduction may also be used.

In accordance with embodiment (c) of the present process, a compound of formula IV is catalytically hydrogenated. In formula IV, the symbol $X^1$ preferably is bromine. The catalytic hydrogenation is conveniently carried out in the presence of a palladium catalyst (e.g. palladium/carbon) at room temperature and atmospheric pressure. The catalytic hydrogenation is terminated after the chlorine or bromine atom denoted by $X^1$ has been removed and before any hydrogenation of the 2,3-double bond or of either of benzylic carbinol groupings occurs.

In accordance with embodiment (d) of the present process, a compound of formula V is treated with a base. Suitable bases for this purpose are alkali metal hydroxides such as sodium hydroxide and potassium hydroxide. This treatment is preferably carried out using alcoholic or aqueous-alcoholic potassium hydroxide at about room temperature.

The oxidation of a compound of formula I in which A is hydroxymethyl in accordance with embodiment (e) of the present process is expediently carried out using chromium trioxide in a solvent such as pyridine, glacial acetic acid, acetone, water or the like or in a mixture of such solvents. The oxidation is preferably carried out in aqueous acetone using chromium trioxide/sulphuric acid. A suitable temperature for this oxidation is between about −20°C and room temperature.

The starting materials of formula II hereinbefore can be prepared in accordance with the following scheme in which R, $R^1$ and X are as above and $X^2$ is chlorine or bromine.

In step (i) a compound of the formula VII

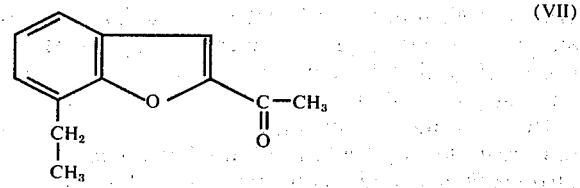

(VII)

is ketalized using ethyleneglycol in the presence of paratoluenesulphonic acid and in the presence of a suitable organic solvent such as an aromatic hydrocarbon (e.g. toluene) to give the ethylene ketal of formula VIII.

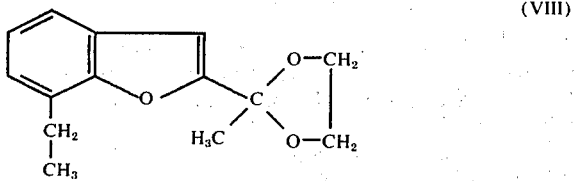

(VIII)

This ethylene ketal is then reacted in step (ii) with N-(chloro or bromo) succinimide, preferably N-bromosuccinimide in the presence of an inert organic solvent (e.g. a chlorinated hydrocarbon such as carbon tetrachloride), to give a compound of formula IX

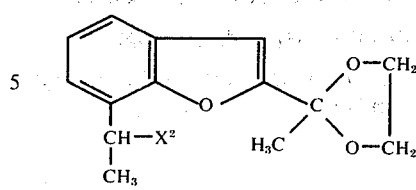

(IX)

This compound in step (iii) is reacted, preferably in situ, with an appropriate lower alkanoic acid (e.g. acetic acid) in the presence of the corresponding alkali metal acylate (e.g. sodium acetate) to give a compound of formula X

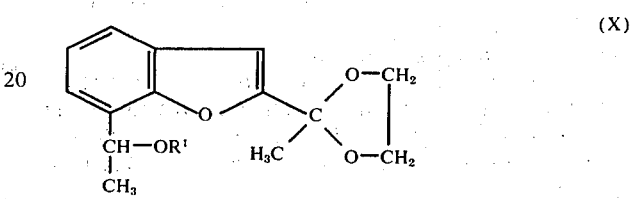

(X)

A compound of formula X is then de-ketalized in step (iv) using an appropriate aromatic sulphonic acid (e.g. benzenesulphonic acid) in a ketonic solvent (preferably ketone such as acetone). The resulting compound of formula XI

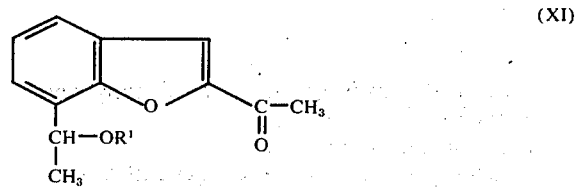

(XI)

is subsequently chlorinated or brominated in step (v) by means of sulphuryl chloride, bromine in an inert organic solvent such as an ether, cuprous bromide in ethyl acetate/chloroform or, preferably, trimethylphenylammonium tribromide in tetrahydrofuran to give a haloketone of formula XII

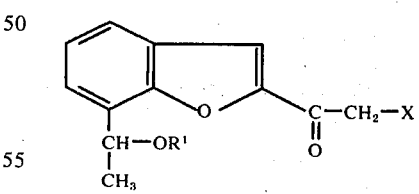

(XII)

A haloketone of formula XII is then reduced with an alkali metal cyanoborohydride (e.g. sodium cyanoborohydride) in an inert organic solvent (e.g. a lower alkanol such as methanol) under acidic conditions, preferably at pH 4, to give a desired starting material of formula II in which R is lower alkanoyl. Alternatively, a haloketone of formula XII is reduced with an alkali metal borohydride in the presence of a lower alkanol (e.g. ethanol) to give a desired starting material of formula II in which R is hydrogen.

The starting materials of formula III hereinbefore can be prepared by reacting a halohydrin of formula XII hereinbefore with tertbutylamine in the presence of an inert organic solvent such as an ether (e.g. diethyl ether, tetrahydrofuran or dioxane).

The starting materials of formula IV hereinbefore can be prepared in accordance with the following scheme in which R, $R^1$, X, $X^1$ and $X^2$ are as above.

Steps (i) to (v) thereof can be carried out in an analogous manner to that described earlier in steps (i) to (v) of the scheme relating to the preparation of starting materials of formula II. A haloketone of formula XVIII

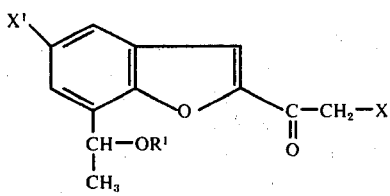

XVIII obtained according to step (v) of the present scheme can be converted into a desired starting material of formula IV by two routes. In one route, said haloketone is reacted in step (vi) with tertbutylamine in the presence of an inert organic solvent such as an ether (e.g. diethyl ether, tetrahydrofuran or dioxane) and the resulting compound of formula XIX

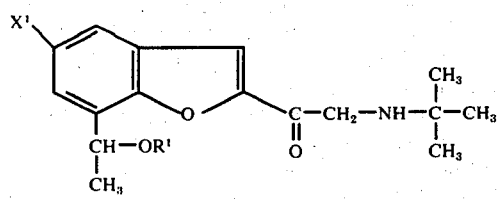

XIX is reduced with an alkali metal borohydride (e.g. sodium borohydride) in the presence of a lower alkanol (e.g. ethanol). In the alternative route, said haloketone is reduced in step (vii) to give a compound of formula XX

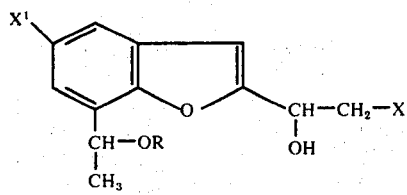

XX

This reduction can be carried out using an alkali metal cyanoborohydride or an alkali-metal borohydride in the same manner as described earlier in connection with the reduction of a compound of formula XII. The resulting compound of formula XX is then reacted with tertbutylamine in the same manner as described in connection with embodiment (a) of the present process. In the alternative route just described there is obtained, as a rule, a mixture containing the desired starting material of formula IV and a compound of the formula

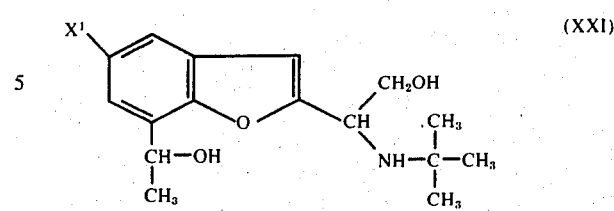

(XXI)

wherein $X^1$ is as above.

This mixture can readily be separated into its components according to conventional techniques; for example, by fractional crystallization of appropriate salts such as the oxalates.

The starting materials of formula V hereinbefore can be prepared, for example, by reacting a compound of formula I hereinbefore in which A is hydroxymethylene, with phosgene, conveniently in the presence of an inert organic solvent such as an aromatic hydrocarbon (e.g. toluene), to give an oxazolidone of the formula

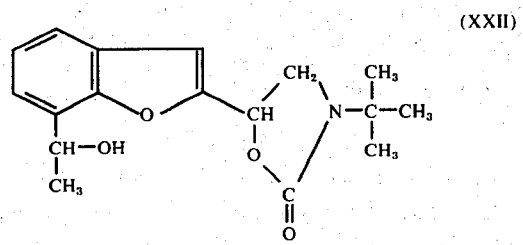

(XXII)

and oxidizing this oxazolidone, for example, with manganese dioxide, suitably in the presence of an inert organic solvent such as a halogenated hydrocarbon (e.g. chloroform, carbon tetrachloride etc).

The compounds of formula I hereinbefore can be converted into acid addition salts by treatment with inorganic acids (e.g. hydrochloric acid, hydrobromic acid, sulphuric acid etc) and organic acids (e.g. acetic acid, tartaric acid, citric acid, maleic acid, oxalic acid, benzoic acid, paratoluenesulphonic acid etc). Pharmaceutically acceptable acid addition salts are preferred.

The benzofuran derivatives provided by the present invention (i.e. the compounds of formula I and their acid addition salts) possess $\beta$-adrenergic blocking activity. Thus they are useful in the treatment of prophylaxis of heart disease such as angina pectoris and cardiac anythmias and in the treatment of hypertension and phaeochromocytoma.

The $\beta$-adrenergic blocking activity of the present benzofuran derivatives can be demonstrated by well-known procedures. In one procedure, 0.05 $\mu$g of isoprenaline is administered intravenously to mice and the increase in heart rate thereby produced is challenged by the intraperitoneal administration of the substance to be tested. The dosage of test substance required to reduce by 50% the increase in heart rate is recorded as the $PD_{50}$. When the hydrogen oxalate of 7-(1'-hydroxyethyl)-$\alpha$-(tertbutylaminomethyl)-2-benzofuranmethanol, which has a $LD_{50}$ of 200-800 mg/kg p.o. in the mouse, is used as the test substance in the foregoing procedure, a $PD_{50}$ of 0.08 mg/kg is recorded. Also, the neutral oxalate of 7-acetyl-$\alpha$-(tertbutylaminomethyl)-2-benzofuranmethanol, which has a $LD_{50}$ of 200-800 mg/kg p.o. in the mouse, shows a $PD_{50}$ of 0.20 mg/kg in the procedure described earlier.

The compounds of formula I and their pharmaceutically acceptable acid addition salts may be used as medicaments in the form of pharmaceutical preparations which contain them in association with a compatible pharmaceutical carrier. This carrier may be an organic or inorganic carrier material suitable for enteral (e.g. oral) or parenteral administration. Examples of such carrier materials are water, gelatine, lactose, starches, gum arabic, magnesium stearate, talc, vegetable oils, refined petroleum jelly and the like. The pharmaceutical preparations can be made up in a solid form (e.g. as tablets, dragees, suppositories or capsules) or in a liquid form (e.g. as solutions, suspensions or emulsions). The pharmaceutical preparations may be sterilized and/or may contain adjuvants such as preservatives, stabilizers, emulsifiers, wetting agents, salts for varying the osmotic pressure or buffers.

The dosages in which the compounds of formula I and their pharmaceutically acceptable acid addition salts can be administered can be varied according to the condition to be treated and upon the directions of the attending physician. In general, however, an amount of from 0.75 mg/kg body weight to 1.25 mg/kg body weight, preferably 1.0 mg/kg body weight, will be administered daily in a single dose or in divided doses.

EXAMPLE 1

A. The preparation of the starting material

A mixture of 80.1 g of 2-acetyl-5-bromo-7-ethylbenzofuran, 37.5 g of triethylamine and 5 g of 5% palladium-on-carbon in 1300 ml of methanol was hydrogenated at room temperature and atmospheric pressure until 1 molar equivalent of hydrogen had been absorbed. The catalyst was filtered off and the filtrate evaporated to dryness. The residual solid was dissolved in ethyl acetate, the resulting solution washed with water and with brine and dried over anhydrous sodium sulphate. The sodium sulphate was then filtered off and the filtrate evaporated under reduced pressure. The residual solid was crystallized from petroleum ether (boiling range 60°–80°C) to give 48.7 g of 2-acetyl-7-ethylbenzofuran as a white crystalline solid of melting point 59°–60°C.

A stirred mixture of 50 g of 2-acetyl-7-ethylbenzofuran, 3.0 g of paratoluenesulphonic acid and 45.0 g of ethyleneglycol in 1200 ml of toluene was heated under reflux for 12 hours with azeotropic removal of water. The cooled solution was washed successively with dilute sodium hydroxide solution, water and brine and then dried over anhydrous sodium sulphate. The sodium sulphate was filtered off and the filtrate evaporated to dryness. The residual yellow oil was distilled under nitrogen to give 48.6 g of 7-ethyl-2-(2-methyl-1,3-dioxolan-2-yl)benzofuran of boiling point 86°–88°C/0.05 mm Hg.

28.0 g of recrystallized N-bromosuccinimide were added to a solution of 32.5 g of 7-ethyl-2-(2-methyl-1,3-dioxolan-2-yl)benzofuran in 480 ml of carbon tetrachloride. The resulting suspension was stirred and heated under reflux for 12 hours. The mixture was cooled overnight at 0°C, precipitated succinimide was filtered off and the filtrate was evaporated at 30°C under reduced pressure. There was thus obtained crude 7-(1'-bromoethyl)-2-(2-methyl-1,3-dioxolan-2-yl)benzofuran which was used immediately in the next stage. The structure of this compound was confirmed by spectral data.

60 g of anhydrous sodium acetate were added to a solution of 43 g of crude 7-(1'-bromoethyl)-2-(2-methyl-1,3-dioxolan-2-yl)benzofuran in 600 ml of glacial acetic acid. The stirred mixture was heated at 60°C for 5 hours, allowed to cool and then poured into 6000 ml of water. The product was extracted with diethyl ether, the extracts were washed three times with water and then with brine and subsequently dried over anhydrous sodium sulphate. The sodium sulphate was filtered off and the filtrate evaporated to dryness under reduced pressure. There was thus obtained 7-(1'-acetoxyethyl)-2-(2-methyl-1,3-dioxolan-2-yl)benzofuran in the form of an oil which was used in the next stage without further purification.

Ca 30 g of crude 7-(1'-acetoxyethyl)-2-(2-methyl-1,3-dioxolan-2-yl) benzofuran were dissolved in 200 ml of acetone and 2 ml of a 33% aqueous solution of benzenesulphonic acid were added to the solution obtained. The resulting solution was heated under reflux for 3 hours, then cooled and evaporated to dryness under reduced pressure. The residual oil was dissolved in diethyl ether and the solution washed with water and with brine and then dried over anhydrous sodium sulphate. The sodium sulphate was then filtered off and the filtrate evaporated to dryness under reduced pressure. The product was purified by column chromatography on silica gel followed by crystallization from cyclohexane to give 2-acetyl-7-(1'-acetoxyethyl)benzofuran in the form of a cream crystalline solid of melting point 82°–83°C.

25.1 g of trimethylphenylammonium tribromide were added at 20°–25°C to a stirred solution of 16.4 g of 2-acetyl-7-(1'-acetoxyethyl)benzofuran in 250 ml of dry tetrahydrofuran. The resulting solution was stirred for 6 hours in order to complete the precipitation of trimethylphenylammonium monobromide. The mixture was poured into 1000 ml of water to which sodium chloride was added to saturation. The product was extracted with diethyl ether, the combined diethyl ether extracts were washed with water and with brine and dried over anhydrous sodium sulphate. The sodium sulphate was filtered off and the filtrate evaporated to dryness. The residual solid was crystallized from diethyl ether to give 8.7 g of 7-(1'-acetoxyethyl)-2-bromoacetylbenzofuran in the form of pale yellow crystals of melting point 86°–88°C.

To a stirred solution of 1.625 g of 7-(1'-acetoxyethyl)-2-bromoacetylbenzofuran in 50 ml of methanol was added methanolic hydrogen chloride to pH 4 and then 0.375 g of sodium cyanoborohydride. The mixture was stirred for 18 hours at 20°–25°C, 50 ml of water were then added and the methanol was evaporated off under reduced pressure. The resulting 7-(1'-acetoxyethyl)-2-(1'-hydroxy-2'-bromoethyl)benzofuran was extracted with diethyl ether, the diethyl ether extract washed with water and with brine and dried over anhydrous sodium sulphate. The sodium sulphate was filtered off and the filtrate evaporated under reduced pressure to give the aforementioned bromohydrin as a dark oil which was used without further purification in the process.

B. The process 5.0 g of tertbutylamine were added to a solution of ca 1.6 g of crude 7-(1'-acetoxyethyl)-2-(1'-hydroxy-2'-bromoethyl)benzofuran in 50 ml of acetonitrile and the clear solution obtained was heated under reflux for 16 hours. The cooled mixture was evaporated to dryness under reduced pressure and the residue partitioned between diethyl ether and dilute sodium hydroxide solution. The diethyl ether layer was extracted twice with dilute hydrochloric acid, the acid extracts were basified with aqueous sodium hydroxide solution and extracted twice with diethyl ether. The combined diethyl ether extracts were washed with water and with brine and dried over anhydrous sodium sulphate. The sodium sulphate was filtered off and the filtrate evaporated under reduced pressure to leave viscous oil. Treatment of the residue in isopropanol with oxalic acid followed by fractional crystallization gave the hydrogen oxalate of 7-(1'-hydroxyethyl)-α-(tertbutylaminomethyl)-2-benzofuranmethanol of melting point 115°C as well as the hydrogen oxalate of the compound of formula VI hereinbefore of melting point 184°–186°C.

EXAMPLE 2

A. The preparation of the starting material 0.9 g of tertbutylamine was added dropwise at 10°C at a stirred solution of 0.975 g of 7-(1'-acetoxyethyl)-2-bromoacetylbenzofuran (prepared as described in the penultimate paragraph of part A of Example 1) in 20 ml of dry diethyl ether. The mixture was then allowed to stand at 0°C for 20 hours. The cold solution was filtered and the filtrate extracted with dilute hydrochloric acid. The acidic extract was made basic with dilute aqueous sodium hydroxide solution and extracted twice with diethyl ether. The combined extracts were washed with water and with brine and then dried over anhydrous sodium sulphate. The sodium sulphate was filtered off, the filtrate evaporated to dryness under reduced pressure and the crude, unstable 7-(1'-acetoxyethyl)-2-benzofuranyl, (tertbutylaminomethyl) ketone obtained was used in the process without further purification.

B. The process

The crude 7-(1'-acetoxyethyl)-2-benzofuranyl, (tertbutylaminomethyl)-ketone prepared as described in part A of this Example was dissolved in 15 ml of absolute ethanol, the solution was stirred and 0.2 g of sodium borohydride was added thereto. The mixture was stirred at 20°–25°C for 20 hours, 30 ml of water were then added and the ethanol was removed by evaporation under reduced pressure. The residue was extracted with diethyl ether, the diethyl ether extracts were washed with water and with brine and then dried over anhydrous sodium sulphate. The sodium sulphate was filtered off and the filtrate evaporated under reduced pressure to give a viscous oil. Treatment of this oil in isopropanol with oxalic acid gave the crystalline hydrogen oxalate of 7-(1'-hydroxyethyl)-α-(tertbutylaminomethyl)-2-benzofuranmethanol of melting point 115°C.

EXAMPLE 3

To a stirred solution of 1.7 g of 7-(1'-hydroxyethyl)-α-(tertbutylaminomethyl)-2-benzofuranmethanol in 20 ml of acetone at 25°C was added dropwise a solution of 3.2 ml of chromium trioxide in dilute sulphuric acid [Jones' reagent] prepared by dissolving 2.667 g of chromium trioxide in a mixture of 2.3 ml of concentrated sulphuric acid and 7.7 ml of water. After 5 minutes, 1 ml of methanol was added followed by 50 ml of water. The mixture was then basified with dilute sodium hydroxide solution and extracted twice with diethyl ether. The combined diethyl ether extracts were washed with water and dried over anhydrous magnesium sulphate. The drying agent was filtered off and the filtrate was evaporated to dryness. The residue was dissolved in isopropanol and treated with an excess of oxalic acid in isopropanol to yield the crystalline neutral oxalate of 7-acetyl-α-(tertbutylaminomethyl)-2-benzofuranmethanol of melting point 220°–221°C.

The following Examples illustrate typical pharmaceutical preparations containing the benzofuran derivatives provided by this invention:

EXAMPLE A

Tablets containing the following ingredients are prepared in the usual manner:

| | |
|---|---|
| Benzofuran derivative | 45.60 mg |
| Lactose | 116.54 mg |
| Maize starch | 78.00 mg |
| Talc | 8.00 mg |
| Magnesium stearate | 1.86 mg |
| | Tablet weight: 250.00 mg |

EXAMPLE B

An ampoule containing the following ingredients was prepared in the usual manner:

| | |
|---|---|
| Benzofuran derivative | 5.697 mg |
| Disodium hydrogen phosphate | 2.550 mg |
| Citric acid monohydrate | 8.405 mg |
| Water ad | 5.000 ml |

We claim:
1. A compound of the formula

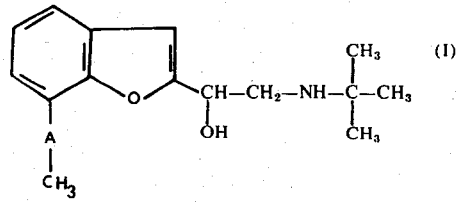

, wherein A is hydroxymethylene or carbonyl, and pharmaceutically acceptable acid addition salts thereof.

2. The compound of claim 1 which is 7-(1'-hydroxyethyl)-α-(tertbutylaminomethyl)-2-benzofuranmethanol.

3. The compound of claim 1 which is 7-acetyl-α-(tertbutylaminomethyl)-2-benzofuranmethanol.

4. A compound of the formula

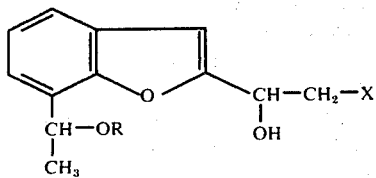
(II)
wherein R is hydrogen or lower alkanoyl and X is chlorine or bromine.
5. The compound of claim 4 which is 7-(1′-acetoxyethyl)-2-(1′-hydroxy-2′-bromoethyl)benzofuran.
6. A compound of the formula
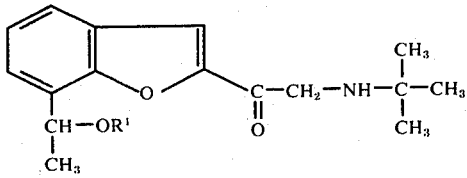
(III)
wherein $R^1$ is lower alkanoyl.
7. The compound of claim 6 which is 7-(1′-acetoxyethyl)-2-benzofuranyl, (tertbutylaminomethyl)-ketone.
* * * * *